United States Patent [19]

Sato et al.

[11] Patent Number: 5,610,016
[45] Date of Patent: Mar. 11, 1997

[54] METHOD FOR MEASURING ADENYL GROUP-CONTAINING SUBSTANCES USING HETEROPOLY-ACID

[75] Inventors: Naofumi Sato; Kamon Shirakawa, both of Saitama, Japan

[73] Assignee: Mochida Pharmaceutical Co., Ltd., Tokyo, Japan

[21] Appl. No.: 413,279

[22] Filed: Mar. 30, 1995

[30] Foreign Application Priority Data

Mar. 30, 1994 [JP] Japan .................................. 6-084085

[51] Int. Cl.$^6$ .............................. C12Q 1/68; C12P 19/24; C07H 21/04; G01T 1/20
[52] U.S. Cl. ................................ 435/6; 435/94; 435/968; 250/361 R; 536/24.3
[58] Field of Search .................................. 436/94; 435/6, 435/968; 250/361; 536/243

[56] References Cited

FOREIGN PATENT DOCUMENTS 0617283  9/1994  European Pat. Off. .

OTHER PUBLICATIONS

Nayak et al, "Liquid phase isomerization of C6–C8 alkenes on heteropolyoxometalates", Applied Catalysis 36:127–137 1988.

Misono et al, "Catalysis by heteropoly compounds. III. The structure and properties of 12 heteropolyacids of molybdenum and tungsten and their salts pertinant to heterogenous catalysis", Bull. Chem. Soc. Jpn. 55:400–406 1982.

Abstract of Lukovskaya, N. et al., "Chemiluminescence reactions with luminol . . . ", Chem. Abstracts vol. 88, p. 609, abstr. No. 83093y, 1978.

Chan–Curtis et al, (1970), "Chemical studies on an acriflavine–phosphotungstate complex; staining of phage deoxyribonucleic acid molecules for the electron microscope", J. Histochem. Cytochem. 18(9):628–634.

Peats et al, (1983), "A sensitive procedure for silver staining proteins in agarose gels", Biotechniques 1(3):154–156.

Kuroda et al, 41st Annual Meeting of The Japan Society of Analytical Chemistry, p. 472 (Aug. 27, 1992).

Kuroda, The 41st Conferences of The Japan Society for Analytical Chemistry at Doshisha University, Sep. 11–13, 1992.

Kuroda et al, Analytica Chimica Acta, vol. 278, pp. 275–278 (1993).

Kai et al, Analytica Chimica Acta, vol. 287, pp. 75–81 (1994).

*Primary Examiner*—Bradley L. Sisson
*Assistant Examiner*—Jeffrey Fredman

[57] ABSTRACT

The invention provides an assay by which detection and/or quantitation of adenyl group-containing substances can be performed simply, with high sensitivity and high signal-to-noise ratio. In particular, the method provides an assay in which the chemiluminescence of a chemiluminescent substance, made by reacting a glyoxal derivative with an adenyl group in the substance to be detected/quantitated in the presence of a heteropolyacid or a heteropolyacid salt, is measured.

13 Claims, 14 Drawing Sheets

0  0.01  0.1   1    10   100  1000  pg/sample

← PCR products
   (5 μl PCR solution/lane)

METHOD FOR MEASURING ADENYL GROUP-CONTAINING SUBSTANCES USING HETEROPOLY-ACID

FIELD OF THE INVENTION

This invention relates to a method for the measurement of adenyl group-containing substances. More particularly, it relates to a method in which an adenyl group in a substance to be measured is chemically modified and the substance is then measured qualitatively or quantitatively by measuring a resulting chemiluminescence of the modified substance.

BACKGROUND OF THE INVENTION

Adenine, adenosine, adenosine phosphate compounds, DNA, RNA and the like are known as adenyl group-containing substances which take important roles in the living body as composing elements of coenzymes, high-energy phosphate compounds, genes and the like.

In general, measurement of adenine and adenosine by separating them from other nucleic acid bases such as guanine, guanosine and the like is carried out making use of chromatographic separation techniques, generally using high performance liquid chromatography.

On the other hand, measurement of nucleic acids is carried out generally making use-of their ultraviolet absorption in the vicinity of 260 nm. In recent years, an ethidium bromide-aided fluorochrome technique has been developed.

Measurement of a target nucleic acid in samples to be tested is carried out using its complementary nucleic acid which is directly or indirectly labeled with a marker such as a radioactive isotope, an enzyme, a fluorescent material, a chemiluminescent substance or the like.

In a method in which a target nucleic acid in a sample to be tested is detected by a nucleic acid amplification technique making use of a polymerase, detection of the amplified nucleic acid is carried out by employing a combination of a nucleic acid electrophoresis and an ethidium bromide-aided fluorochrome technique.

In addition, specific affinity of an antibody for its corresponding antigen is used in immunological assay methods which are divided into methods in which the immunologicat reaction is directly detected as precipitation or turbidity of the resulting antigen-antibody complex and methods in which the antibody or antigen is labeled with a marker for use in the measurement. In the latter case, a radioactive isotope, an enzyme, a fluorescent material, a chemiluminescent substance and the like are used as markers, and the measurement can be effected with greater sensitivity of detector than in the former case. In recent years, a high sensitivity assay method has been developed in which an antibody is labeled with a nucleic acid and used in combination with a polymerase-aided nucleic acid amplification technique. Also in this method, an ethidium bromide-aided fluorochrome technique is used in its final step for the detection of amplified nucleic acid.

Kuroda et al. have reported at the 41th Annual Meeting of The Japan Society of Analytical Chemistry that quantitative determination of adenine can be attained by a method in which a luminescent substance is derived by allowing phenylglyoxal to react with adenine in the presence of hydrochloric acid, emission from the resulting chemiluminescent substance is effected by adding sodium hydroxide aqueous solution to the reaction solution in the presence of $H_2O_2$ and then the resulting luminescence activity is measured.

Though this method has disadvantages of causing a high background value in the absence of adenine and its low emission quantity per adenine, it is useful from a viewpoint that it can effect adenine-specific measurement easily without requiring complex separation purification steps which are essential in the aforementioned assay methods.

On the other hand, heteropoly-acids and their salts are used as catalysts, to provide strong acidity and oxidation potential. They are used in a variety of reactions such as oxidation of hydrocarbons, polymerization and epoxidation of alkenes and the like.

The aforementioned assay methods have the following disadvantages.

The method in which adenine and adenosine in a test sample are measured by employing a separation step making use of a chromatography step requires complex handling and additional equipment such as high performance liquid chromatographys. In addition, when an adenine-containing substance is measured, it is necessary to employ a pre-treatment step in order to decompose the adenine-containing substance into adenine or adenosine.

The nucleic acid measuring method which uses ultraviolet absorption in the vicinity of 260 nm has disadvantages in terms of its measuring sensitivity and specificity.

The nucleic acid measuring method by an ethidium bromide-aided fluorochrome technique requires special care in handling, because the fluorescence intensity fluctuates extensively between single-stranded and double-stranded nucleic acids, and ethidium bromide is a strongly carcinogenic substance.

In the nucleic acid measuring method in which a complementary nucleic acid is directly or indirectly labeled, and a target nucleic acid in a sample is hybridized to the complementary nucleic acid, it is necessary to devise a special means with regard to the labeling position and the like when the complementary nucleic acid is labeled so that binding of the target nucleic acid and the complementary nucleic acid is not spoiled.

Even in the cases of the method in which a target nucleic acid in a sample is detected by a polymerase-aided nucleic acid amplification technique and the method in which high sensitivity measurement is effected by labeling an antibody with a nucleic acid by means of an immunoassay technique and then using a nucleic acid amplification technique, it is necessary to use ethidium bromide in their final detection step, hence posing the aforementioned problems.

It is accordingly a primary object of the present invention to resolve one or more of these problems.

SUMMARY OF THE INVENTION

With the aim of overcoming the aforementioned problems involved in the prior art, the inventors of the present invention have conducted intensive studies and found a new measuring method in which a chemiluminescent substance is derived by allowing a glyoxal derivative represented by the following formula 1 to react with the adenyl group in a substance to be measured in the presence of a heteropoly-acid or a heteropoly-acid salt, and the amount of the adenyl group-containing substance is measured with a high sensitivity based on the luminescence quantity of the luminescent substance. The present invention has been accomplished on the basis of this finding.

Accordingly, the present invention provides a method for the measurement of adenyl group-containing substances which comprises deriving a chemiluminescent substance by allowing a glyoxal derivative represented by the following formula 1 to react with the adenyl group in a substance to be measured in the presence of a heteropoly-acid or a heteropoly-acid salt and measuring the amount of substance to be measured using a luminescence activity obtained from the chemiluminescent substance.

The present invention provides a method for the measurement of adenyl group-containing substances according to the above method wherein the heteropoly-acid or heteropoly-acid salt is tungstosilicic acid, tungstophosphoric acid, tungstoarsenic acid, tungstogermanic acid, molybdosilicic acid, molybdophosphoric acid, molybdoarsenic acid, molybdogermanic acid, vanadophosphoric acid or a salt thereof.

Preferably, the heteropoly-acid or heteropoly-acid salt is a compound selected from the group consisting of tungstosilicic acid, tungstophosphoric acid, tungstoarsenic acid, molybdosilicic acid, molybdophosphoric acid, molybdoarsenic acid and molybdophosphoric acid sodium salt.

More preferably, the heteropoly-acid or heteropoly-acid salt is a compound selected from the group consisting of tungstosilicic acid, tungstophosphoric acid, molybdophosphoric acid and molybdophosphoric acid sodium salt.

This invention also provides a method for the measurement of adenyl group-containing substances according to the above method wherein the glyoxal derivative is represented by the following formula (1):

$$R^1-CO-R^2 \tag{1}$$

wherein $R^1$ is a hydrogen atom; an alkyl group, an alkenyl group or an alkynyl group having 1 to 12 carbon atoms; or an aryl group or an aromatic heterocyclic group having 1 to 18 carbon atoms, which may have a substituent group that may also form a condensed ring, $R^2$ is an aldehyde group or a group represented by —CH(XR$^3$) (X'R$^4$) in which X and X' are the same or different groups selected from an oxygen atom, a sulfoxide group, a sulfone group, a sulfur atom, a selenoxide group and a selenium atom, and $R^3$ and $R^4$ are the same or different groups which may form a ring by binding and are selected from a hydrogen atom; an alkyl group, an alkenyl group or an alkynyl group having 1 to 12 carbon atoms; and an aryl group having 1 to 16 carbon atoms, which may have a substituent group that may also form a condensed ring.

In a preferred glyoxal derivative, $R^1$ is a hydrogen atom; an alkyl group having 1 to 8 carbon atoms; or a phenyl group or an aromatic heterocyclic group having 1 to 8 carbon atoms, which may have a substituent group that may also form a condensed ring, $R^2$ is an aldehyde group or a group represented by —CH(XR$^3$)(X'R$^4$) where X and X' are the same or different from each other and each represents an oxygen atom or a sulfur atom, and $R^3$ and $R^4$ are the same or different groups which may form a ring by binding and are selected from a hydrogen atom; an alkyl group having 1 to 4 carbon atoms or a phenyl group, which may have a substituent group that may also form a condensed ring.

Preferably, the glyoxal derivative is a compound selected from the group consisting of methylglyoxal, methylglyoxal dimethylacetal, ethylglyoxal dimethylacetal, n-butylglyoxal dimethylacetal, n-octylglyoxal dimethylacetal, phenylglyoxal, phenylglyoxal dimethylacetal, p-methylphenylglyoxal and p-fluorophenylglyoxal.

This invention also provides a method for the measurement of adenyl group-containing substances according to the above method wherein the substance to be measured is adenine, adenosine, an adenosine phosphate compound, DNA or RNA.

It also provides a method for the measurement of adenyl group-containing substances according to the above method wherein the luminescence activity of the chemiluminescent substance is measured by adding a reaction initiator to the reaction system in the presence of a "luminescence solvent." A luminescence solvent is a solvent appropriate for conducting a chemiluminescent reaction.

Preferably, the luminescence solvent is a solvent selected from the group consisting of dimethylformamide, isopropanol, acetonitrile, dioxane and dimethyl sulfoxide.

This invention also provides a method for the measurement of adenyl group-containing substances wherein the substance to be measured is a target nucleic acid and/or an amplified product thereof bound to a complementary nucleic acid of a capture probe capable of undergoing complementary binding to the target nucleic acid.

This invention also provides a method for the measurement of adenyl group-containing substances method wherein the substance to be measured is a target nucleic acid and/or an amplified product thereof wherein the target nucleic acid in a sample is detected by amplifying it by a nucleic acid amplification method.

The present invention also provides a method for the measurement of adenyl group-containing substances wherein the substance to be measured is an amplified product obtained by a nucleic acid amplification method using as a target a nucleic acid or adenyl group-containing substance that labels an antibody labeled or an antigen labeled that is used in an immunological assay method in which a substance to be tested in a sample is detected by its immunological reaction with the labeled antibody or antigen.

This invention also provides a DNA probe method in which a target nucleic acid in a sample is detected using a capture probe capable of complementary binding to the target nucleic acid, which comprises deriving a chemiluminescent substance by allowing a glyoxal derivative represented by the aforementioned formula 1 to react with the adenyl group of the target nucleic acid or of an amplified product thereof in the presence of a heteropoly-acid or a heteropoly-acid salt and measuring the target nucleic acid using a luminescence activity obtained from the chemiluminescent substance as a quantitative or qualitative measure.

It also provides a target nucleic acid measuring method in which a target nucleic acid in a sample is detected by amplifying it by a nucleic acid amplification method, which comprises deriving a chemiluminescent substance by allowing a glyoxal derivative represented by the aforementioned formula 1 to react with the adenyl group of the target nucleic acid or of an amplified product thereof in the presence of a heteropoly-acid or a heteropoly-acid salt and measuring the target nucleic acid using a luminescence activity obtained from the chemiluminescent substance as a quantitative or qualitative measure.

This invention also provides an immunological assay method for the measurement of adenyl group-containing substances in which a substance to be tested in a sample is detected making use of its immunological reaction with a labeled antibody or antigen, which comprises deriving a chemiluminescent substance by allowing a glyoxal derivative represented by the aforementioned formula 1 to react with the adenyl group of an amplified product obtained by a nucleic acid amplification method using as a target nucleic acid an adenyl group-containing substance and/or a nucleic acid that labels said antibody or antigen, or an amplified product obtained by a nucleic acid amplification method using a nucleic acid or an adenyl group-containing substance that labels said antibody or antigen as a substrate for said amplification method. The reaction is conducted in the presence of a heteropoly-acid or a heteropoly-acid salt and the substance to be measured is detected using a luminescence activity obtained from the chemiluminescent substance as a quantitative or qualitative measure.

Other objects and advantages of the present invention will be made apparent as the description progresses.

DETAILED DESCRIPTION OF THE INVENTION

Figure 1:
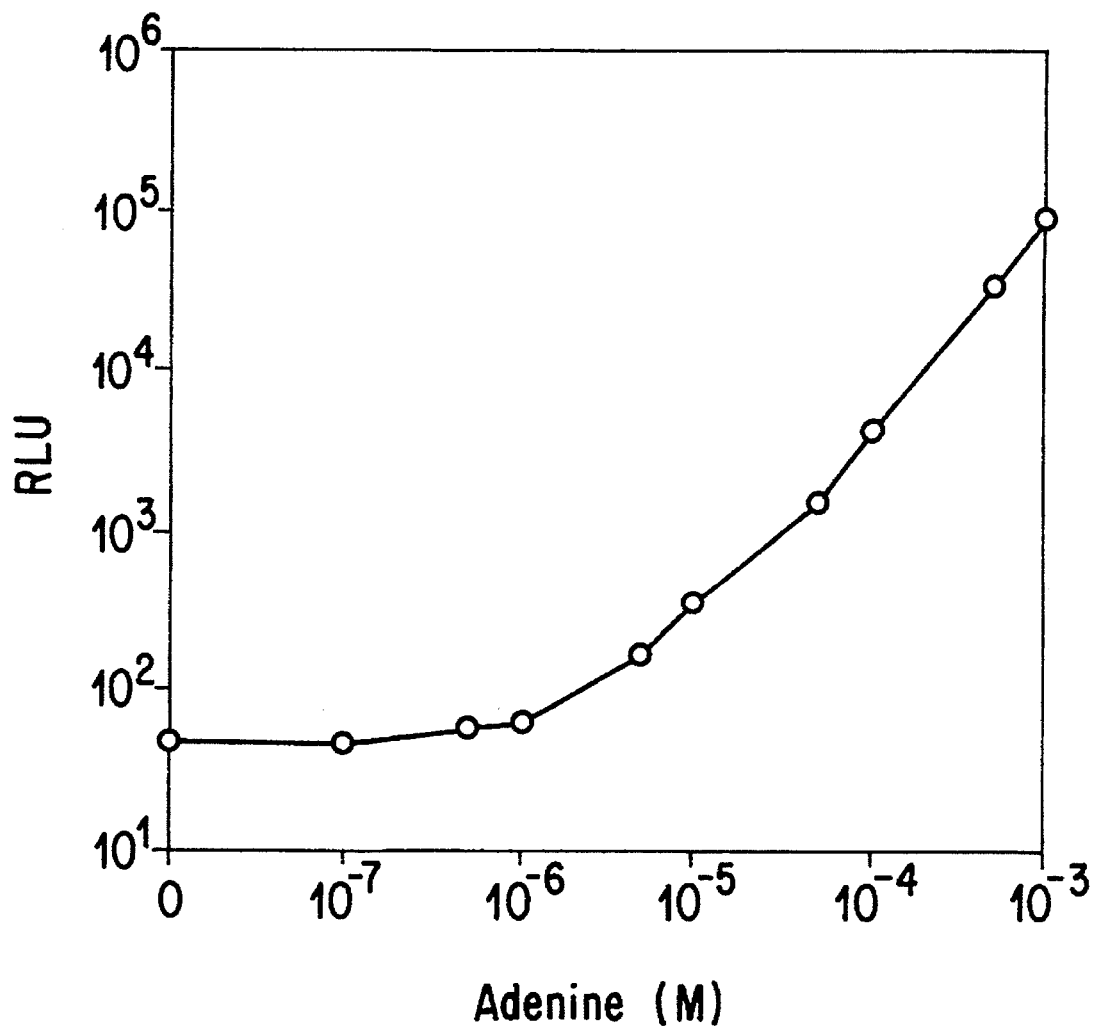
FIG. 1 is a graph showing a calibration curve of adenine when phenylglyoxal is used in the presence of tungstosilicic acid.

The measuring method of the present invention is used for the measurement of particular substance in a sample. Sample materials include blood, body fluid, urine, tissues, microbial culture broths and extracts thereof, as well as polymerase chain reaction (PCR) mixtures.

The substances to be measured by the measuring method of the present invention are adenyl group-containing substances, and typical examples of such substances include adenine, adenosine, adenosine phosphate compounds, DNA, including PCR products, RNA and the like. The inventive method can be applied also to the measurement of adenyl group-containing artificially modified nucleic acids.

In the practice of the measuring method of the present invention, a chemiluminescent substance is first derived by allowing a glyoxal derivative to react with a substance to be measured in the presence of a heteropoly-acid or a heteropoly-acid salt.

Examples of the heteropoly-acid or heteropoly-acid salt include tungstosilicic acid, tungstophosphoric acid, tungstoarsenic acid, tungstogermanic acid, molybdosilicic acid, molybdophosphoric acid, molybdoarsenic acid, molybdogermanic acid and vanadophosphoric acid and their sodium, potassium, ammonium or similar salts.

Preferably, tungstosilicic acid, tungstophosphoric acid, tungstoarsenic acid, molybdosilicic acid, molybdophosphoric acid, molybdoarsenic acid or molybdophosphoric acid sodium salt may be used.

More preferably, good results may be obtained when tungstosilicic acid, tungstophosphoric acid or molybdophosphoric acid or molybdophosphoric acid sodium salt is used.

The heteropoly-acid or heteropoly-acid salt may be used in an amount providing a final concentration in the reaction solution of preferably from 0.001 to 1M, more preferably from 0.003 to 0.2M, most preferably from 0.01 to 0.1M.

The glyoxal derivative to be used in the measuring method of the present invention is a compound represented by the following formula (1) wherein $R^1$ and $R^2$ are groups selected from the following substituent groups.

$$R^1\text{—CO—}R^2 \qquad (1)$$

In the above formula, $R^1$ is a hydrogen atom; an alkyl group, an alkenyl group or an alkynyl group having 1 to 12 carbon atoms; or an aryl group or an aromatic heterocyclic group having 1 to 18 carbon atoms, which may have a substituent group that may also form a condensed ring.

Preferably, $R^1$ is a hydrogen atom; an alkyl group having 1 to 8 carbon atoms; or a phenyl group or an aromatic heterocyclic group having 1 to 8 carbon atoms, which may have a substituent group that may also form a condensed ring.

Illustrative examples of $R^1$ include methyl, ethyl, propyl, butyl, pentyl, hexyl, heptyl, octyl, phenyl, methylphenyl, fluorophenyl, nitrophenyl, methoxyphenyl, furanyl, benzofuranyl and similar groups.

$R^2$ is an aldehyde group or a group represented by the formula (Z): —$CH(XR^3)(X'R^4)$ (Z) groups selected from an oxygen atom, a sulfoxide group, a sulfone group, a sulfur atom, a selenoxide group and a selenium atom.

Preferably, X and X' are the same or different from each other and each represents an oxygen atom or a sulfur atom.

Illustrative examples of $R^2$ include aldehyde, acetal, thioacetal and siumilar groups.

$R^3$ and $R^4$ are the same or different groups which may form a ring by binding and are selected from a hydrogen atom; an alkyl group, an alkenyl group or an alkynyl having 1 to 12 carbon atoms; and an aryl group having 1 to 16 carbon atoms, which may have a substituent group that may also form a condensed ring.

Preferably, $R^3$ and $R^4$ are the same or different groups which may form a ring by binding and are selected from a hydrogen atom; an alkyl group having 1 to 4 carbon atoms or a phenyl group, which may have a substituent group that may also form a condensed ring.

Illustrative examples of $R^3$ and $R^4$ include methyl, ethyl, propyl, butyl and similar groups and an ethylene group as a combined form of $R^3$ and $R^4$ of which a methyl group is particularly preferred in view of its synthetic advantage.

When $R^1$ has a substituent group which may form a condensed ring, at least one group may be selected from the class consisting of a carboxyl group; a hydroxyl group; an amino group; an amide group; a sulfonamide group; a sulfide group; a sulfoxide group; a sulfone group; a nitro group; a halide atom; a mercapto group; an acyl group; an azide group; an alkylamino, alkyl, alkenyl, alkynyl or alkoxy group having 1 to 12 carbon atoms; a polyalkoxy group; an aryl group; an aryloxy group and a heterocyclic group.

When $R^1$ has a substituent group which may form a condensed ring, it is preferable to select at least one group from the class consisting of a carboxyl group; a hydroxyl group; an amino group; a nitro group; a halide atom; a mercapto group; an acetyl group; a benzoyl group; an alkylamino, alkyl, alkenyl or alkoxy group having 1 to 4 carbon atoms; an aryl group and an aryloxy group.

Preferably, the group which substitutes $R^1$ or forms a condensed ring therewith is nitro, fluoro, methoxy, benzoyl, acetyl, amino, methyl or phenyl.

In addition, the group itself which substitutes $R^1$ or forms a condensed ring therewith may further be substituted or form a condensed ring with at least one group selected from the class consisting of a carboxyl group; a hydroxyl group; an amino group; an amide group; a sulfonamide group; a sulfide group; a sulfoxide group; a sulfone group; a nitro group; a halide atom; a mercapto group; an acyl group; an azide group; an alkylamino, alkyl, alkenyl, alkynyl or alkoxy group having 1 to 12 carbon atoms; a polyalkoxy group; an aryl group; an aryloxy group and a heterocyclic group.

When $R^3$ or $R^4$ has a substituent group which may form a condensed ring, at least one group may be selected from the class consisting of a carboxyl group; a hydroxyl group; an amino group; an amide group; a sulfonamide group; a sulfide group; a sulfoxide group; a sulfone group; a nitro group; a halide atom; a mercapto group; an acyl group; an azide group; an alkylamino, alkyl, alkenyl, alkynyl or alkoxy group having 1 to 12 carbon atoms; a polyalkoxy group; an aryl group; an arytoxy group and a heterocyclic group.

When $R^3$ or $R^4$ has a substituent group which may form a condensed ring, it is preferable to select at least one group from the class consisting of a carboxyl group; a hydroxyl group; an amino group; a nitro group; a halide atom; a mercapto group; an acetyl group; a benzoyl group; an alkylamino, alkyl, alkenyl or alkoxy group having 1 to 4 carbon atoms; an aryl group and an aryloxy group.

In addition, the group itself which substitutes $R^3$ or $R^4$ or forms a condensed ring therewith may further be substituted or form a condensed ring with at least one group selected from the class consisting of a carboxyl group; a hydroxyl group; an amino group; an amide group; a sulfonamide group; a sulfide group; a sulfoxide group; a sulfone group; a nitro group; a halide atom; a mercapto group; an acyl group; an azide group; an alkylamino, alkyl, alkenyl, alkynyl or alkoxy group having 1 to 12 carbon atoms; a polyalkoxy group; an aryl group; an aryloxy group and a heterocyclic group.

$R^1$ is a group which exerts influence upon resonance structure of the luminescent substance to be derived and is selected from the aforementioned substituent groups.

$R^2$ which binds directly to an adenyl group, is a group such as an aldehyde group or a group represented by —$CH(XR^3)$ ($X'R^4$) where X, X', $R^3$ and $R^4$ may be selected from the aforementioned substituent groups.

Illustrative examples of the compound represented by the aforementioned formula (1) to be used as the glyoxal derivative in the measuring method of the present invention include methylglyoxal, methylglyoxal dimethylacetal, ethylglyoxal, ethylglyoxal dimethylacetal, n-propylglyoxal, n-propylglyoxal dimethylacetal, n-butylglyoxal, n-butylglyoxal dimethylacetal, n-pentylglyoxal, n-pentylglyoxal dimethylacetal, n-hexylglyoxal, n-hexylglyoxal dimethylacetal, n-heptylglyoxal, n-heptylglyoxal dimethylacetal, n-octylglyoxal, n-octylglyoxal dimethylacetal, phenylglyoxal, phenylglyoxal dimethylacetal, p-methylphenylglyoxal, p-methylphenylglyoxal dimethylacetal, p-fluorophenylglyoxal, p-fluorophenylglyoxal dimethylacetal, p-nitrophenylglyoxal, p-nitrophenylglyoxal dimethylacetal, p-methoxyphenylglyoxal, p-methoxyphenylglyoxal dimethylacetal, 2-benzofuranylglyoxal and 2-benzofuranylglyoxal dimethylacetal.

Particularly preferred examples of the glyoxal derivative include methylglyoxal, methylglyoxal dimethylacetal, ethylglyoxal dimethylacetal, n-butylglyoxal dimethylacetal, n-octylglyoxal, phenylglyoxal, phenylglyoxal dimethylacetal, p-methylphenylglyoxal and p-fluorophenylglyoxal.

According to the measuring method of the present invention, a chemiluminescent substance is derived as a first step by allowing a substance to be measured and a glyoxal derivative to react with each other in the presence of a heteropoly-acid or a heteropoly-acid salt.

The glyoxal derivative may be used in an amount providing a final concentration in the reaction solution, of preferably from 0.01 to 1M, more preferably from 0.05 to 0.2M.

As a solvent to be used in this reaction, generally used polar solvents can be used, but isopropanol (i-PrOH), ethanol or dimethyl sulfoxide (DMSO) is particularly preferred.

The reaction may be carried out at a temperature of preferably from 10° to 150° C., more preferably from 70° to 110° C. for the purpose of completing the reaction quickly.

The reaction may be carried out for 5 to 120 minutes, but a period of from 30 to 90 minutes is particularly preferred from the viewpoint of signal noise ratio (S/N ratio) and luminescence quantity.

Next, a luminescence reaction is carried out by adding a luminescence solvent and a reaction initiator, in that order, to the chemiluminescent substance thus formed by the above reaction or to a reaction solution which contains the chemiluminescent substance, In this instance, a surface active agent may be added optionally to the reaction initiator. Thereafter, the quantity of luminescence of the chemiluminescent reaction is measured.

Generally used polar solvents such as i-PrOH, dimethylformamide (DMF), dioxane, acetonitrile, diglyme, DMSO and the like may be used as the luminescence solvent, of which DMF, i-PrOH, acetonitrile, dioxane and DMSO are particularly preferred.

An oxidizing agent may or may not be used in the measuring method of the present invention, though such an agent is generally required for the luminescence reaction of chemiluminescent substances.

Examples of the oxidizing agent include $H_2O_2$, urea hydrogen peroxide, metal peroxides and the like, of which $H_2O_2$ is preferred.

The amount of $H_2O_2$ when used as the oxidizing agent provides a range of preferably from 0 to 300 mM, more preferably from 5 to 100 mM, of final concentration in the reaction solution.

In addition, the time and quantity of luminescence can be controlled by adding a sulfur compound to the luminescence solvent.

Examples of the sulfur compound include L-cysteine ethyl ester, L-cysteine, 2-mercaptoethanol, hydroxyethyl disulfide, thiodiglycol and the like, of which L-cysteine ethyl ester or L-cysteine is particularly preferred.

The sulfur compound may be added in an amount providing a final concentration of preferably from 0.1 to 300 mM, more preferably from 0.5 to 10 mM, in the reaction solution.

As an initiator of the chemiluminescence reaction, distilled water may be used preferably.

Also, an additive agent such as an alkali solution, a surface active agent or the like may be added to the reaction initiator, for the purpose of controlling luminescence time, luminescence quantity and the like.

When sodium hydroxide aqueous solution is added as an alkali solution to the reaction initiator, luminescence quantity increases by the use of sodium hydroxide at a final concentration of 0.01 to 1N in the reaction solution.

From the viewpoint of signal noise ratio (S/N ratio), it is preferable to measure the luminescence quantity within 5 seconds, particularly 2 seconds, immediately after the addition of the reaction initiator.

Detection of luminescence may be effected by the use of a photon counter, X-ray films and the like, of which a photon counter is desirable because quantitative measurement can be made.

Being specific for an adenyl group, other nucleic acid bases such as thymine, cytosine, guanine, uracil and similar bases and derivatives thereof cause almost no interference in the method of the present invention.

Methylated adenine as a naturally occurring adenine derivative is not detected as it is.

Such a high specificity of the method of the present invention can be used efficiently in a DNA probe method in which a target nucleic acid as a substance to be measured in a sample is hybridized with a capture probe which contains a sequence complementary to the target, and the target nucleic acid is detected in a sequence specific manner.

That is, only the target nucleic acid-originated adenyl group in a test sample can be detected when a capture probe which does not derive a chemiluminescent substance by its reaction with a glyoxal derivative is prepared by 1) designing a capture probe which does not contain an adenyl group, 2) deleting adenyl group-corresponding bases from a capture probe or 3) modifying or substituting adenyl groups in a capture probe into or with a nonreactive group described above, and its reaction product with the test sample is measured by the method of the present invention. The target nucleic acid-originated adenyl group can also be measured by using an adenyl group-containing capture probe as it is and subtracting the capture probe-originated luminescence quantity from the detected luminescence quantity.

While prior art DNA probe techniques require complex handling because a target nucleic acid bound to a capture probe must be further reacted with a labeled probe or a labeled antibody, the DNA probe-aided measuring method of the present invention is an unusually simple and useful method because it can measure a capture probe-bound target nucleic acid directly without using a labeled substance.

For example, a capture probe whose adenine portion is substituted with a cross linking agent such as Uni-Link™ Amino Modifier (Clontech Laboratories, Inc.) is prepared using a DNA synthesizer and immobilized on an amino group-introduced microtiter plate using glutaraldehyde. Thereafter, a target nucleic acid is detected by adding a test sample to the resulting plate to effect the reaction, washing the plate and then measuring the target nucleic acid by the measuring method of the present invention.

The measuring method of the present invention can also be applied to a target nucleic acid measuring method in which a target nucleic acid in a test sample is amplified by a polymerase-aided nucleic acid amplification method such as PCR, and both or either of the target nucleic acid and its amplified product in the resulting reaction solution is measured.

That is, a DNA fragment which has been designed to exclude adenyl groups or inactivated by deletion, modification or substitution of adenyl groups, for the purpose of preventing derivation of a chemiluminescent substance similar to the case of the aforementioned capture probe, is used as an amplification primer of a target nucleic acid. After amplifying the target nucleic acid by PCR using the amplification primer to which biotin, antigen or a similar specific binding substance has been chemically bound (this substance is also designed or modified to prevent derivation of an adenyl group-based chemiluminescent substance in the same manner as the case of the amplification primer), the specific binding substance in the resulting reaction solution is allowed to react with a solid phase on which avidin, streptavidin, antibody or similar substance to be bound to the specific binding substance has been immobilized. After washing, measurement is carried out by the aforementioned method using a compound represented by the aforementioned formula 1 as a glyoxal derivative in the presence of a heteropoly-acid or a heteropoly-acid salt. Since excess primers do not produce luminescence in the measuring system, the luminescence originated from the PCR amplification product of the target nucleic acid can be detected selectively without requiring a step for the separation of the amplified product and primers in the reaction solution by electrophoresis or similar technique after the amplification reaction.

With the advance of nucleic acid amplification techniques including the recently developed PCR, importance of the determination of amplified nucleic acids has been increasing broadly from fundamental biochemical research to clinical application in medical science. The measuring method of the present invention can measure such amplified nucleic acids easily and simply within a short period of time, and, since the measured values depend on the amount of adenyl groups, the inventive method is not affected by the different structures of single-stranded and double-stranded nucleic acids, while such an influence is unavoidable in the case of the prior art fluorochrome technique.

The measuring method of the present invention can be applied to other methods than the detection of nucleic acids.

That is, the amount of a substance to be tested in a sample can be calculated based on the adenine luminescence in the same manner as the case of nucleic acids, when an adenine polymer is used as a marker substance of an antibody or antigen in an immunoassay method in which a substance to be tested in a test sample is detected making use of its immunological reaction. Also, when a nucleic acid is used as a marker substance, the amount of a substance to be tested in a sample can be calculated by amplifying the nucleic acid by PCR and measuring the resulting PCR amplification product based on the adenine luminescence.

For example, measurement of a substance to be tested can be achieved by deriving a chemiluminescent substance by allowing a glyoxal derivative represented by the aforementioned formula 1 to react with adenyl groups in an amplified product in the presence of a heteropoly-acid or a heteropoly-acid salt, and measuring the substance to be tested using a luminescence activity obtained from the chemiluminescent substance as a marker. In this case, the amplified product is obtained by a polymerase-aided nucleic acid amplification technique using a nucleic acid moiety that labels an antibody or nucleic acid labeled with an adenyl group-containing substance or a nucleic acid labeled with a mixture thereof as a target nucleic acid. The amplified product can also be obtained using a nucleic acid moiety that labels an antigen or nucleic acid labeled with an adenyl group-containing substance or a nucleic acid labeled with a mixture thereof as a target nucleic acid.

EXAMPLES

The following examples are provided to further illustrate the present invention. It is to be understood, however, that the examples are for purpose of illustration only and are not to be construed to limit the scope of the invention.

Example 1

Preparation of Adenine Calibration Curve Using Phenylglyoxal

Adenine was dissolved in a small amount of 0.1N hydrochloric acid and made into serial dilutions of from 0 to $1\times10^{-3}$M with i-PrOH. A 100 µl portion of each sample solution having respective concentration thus prepared was put in a glass vial, 50 µl of 0.4M phenylglyoxal and the same volume of 0.196M tungstosilicic acid (dissolved in i-PrOH) were added to the sample solution, and the vial was then sealed and heated at 100° C. for 1 hour. The thus obtained reaction mixture was cooled and used for the measurement of chemiluminescence in the following manner. A 10 µl portion of the reaction mixture was put in a glass tube for measuring use and mixed with 400 µl of DMF containing 50 mM of hydrogen peroxide and 5 mM of cysteine ethyl ester (CysE). After arranging the sample tube for measuring use in a chemiluminescence measuring apparatus (LB952T/16, manufactured by Berthold), 300 µl of distilled water was added to the tube to start the luminescence reaction, and the resulting luminescent activity (RLU) was measured for 2 seconds just after the addition of the reaction initiator.

When a calibration curve of adenine was prepared from the thus obtained luminescence intensity, a satisfactory dose/response curve was obtained within the range of from $1\times10^{-6}$ to $1\times10^{-3}$M as shown in FIG. 1. In the figure, the abscissa indicates adenine concentration, and the ordinate indicates luminescence intensity at each adenine concentration.

Example 2

Preparation of Adenine Calibration Curve Using Methylglyoxal Dimethylacetal

Adenine was dissolved in a small amount of 0.1N hydrochloric acid and made into serial dilutions of from 0 to $1\times10^{-3}$M with i-PrOH. A 100 µl portion of each sample solution having respective concentration was put in a glass vial, followed by the addition of 50 µl of 0.4M methylglyoxal dimethylacetal (MGA) and the same volume of 0.196M tungstosilicic acid (dissolved in i-PrOH), and the vial was then sealed and heated at 100° C. for 1 hour. The thus obtained reaction solution was cooled and used for the measurement of luminescent activity (RLU) in the same manner as described in Example 1.

Figure 2:
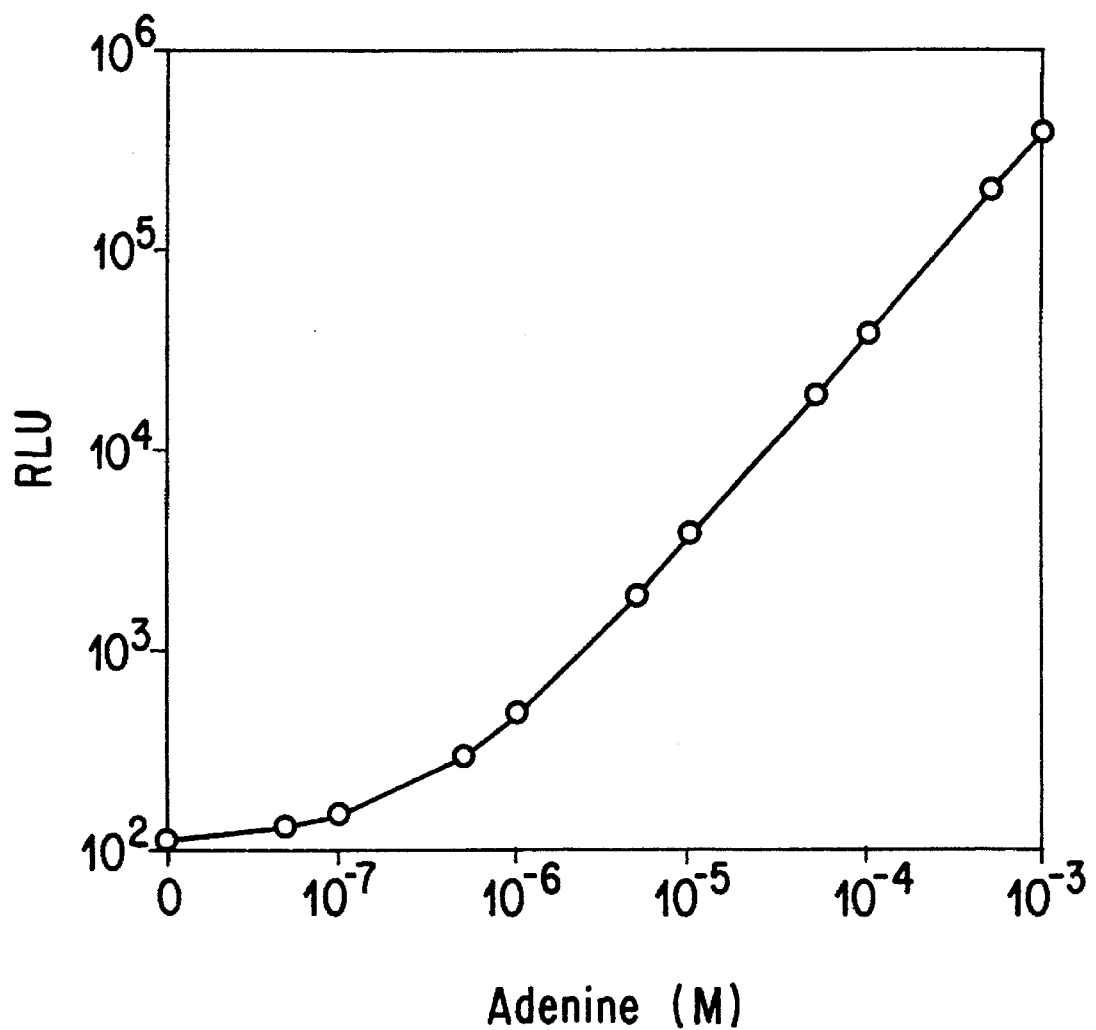
FIG. 2 is a graph showing a calibration curve of adenine when methylglyoxal dimethylacetal is used in the presence of tungstosilicic acid.

When a calibration curve of adenine was prepared from the thus obtained luminescence intensity, a satisfactory dose/response curve was obtained within the range of from $1\times10^{-7}$M to $1\times10^{-3}$M as shown in FIG. 2. In the figure, the abscissa indicates adenine concentration, and the ordinate indicates the luminescence intensity at each adenine concentration.

Example 3

Preparation of Calibration Curves of DNA, poly A and poly dA Using Methylglyoxal Dimethylacetal Each of poly dA (manufactured by Pharmacia), poly A (manufactured by Pharmacia) and DNA (salmon sperm, manufactured by Pharmacia) was dissolved in a small amount of distilled water and made into serial dilutions of from 0 to 0.2 mg/ml with i-PrOH. A 100 µl portion of each sample solution having respective concentration was put in a glass vial, followed by the addition of 50 µl of 0.4M methylglyoxal dimethylacetal (MGA) and the same volume of 0.196M tungstosilicic acid (dissolved in i-PrOH), and the vial was then sealed and heated at 100° C. for 1 hour. The thus obtained reaction mixture was cooled and used for the measurement of luminescent activity (RLU) in the same manner as described in Example 1.

Figure 3:
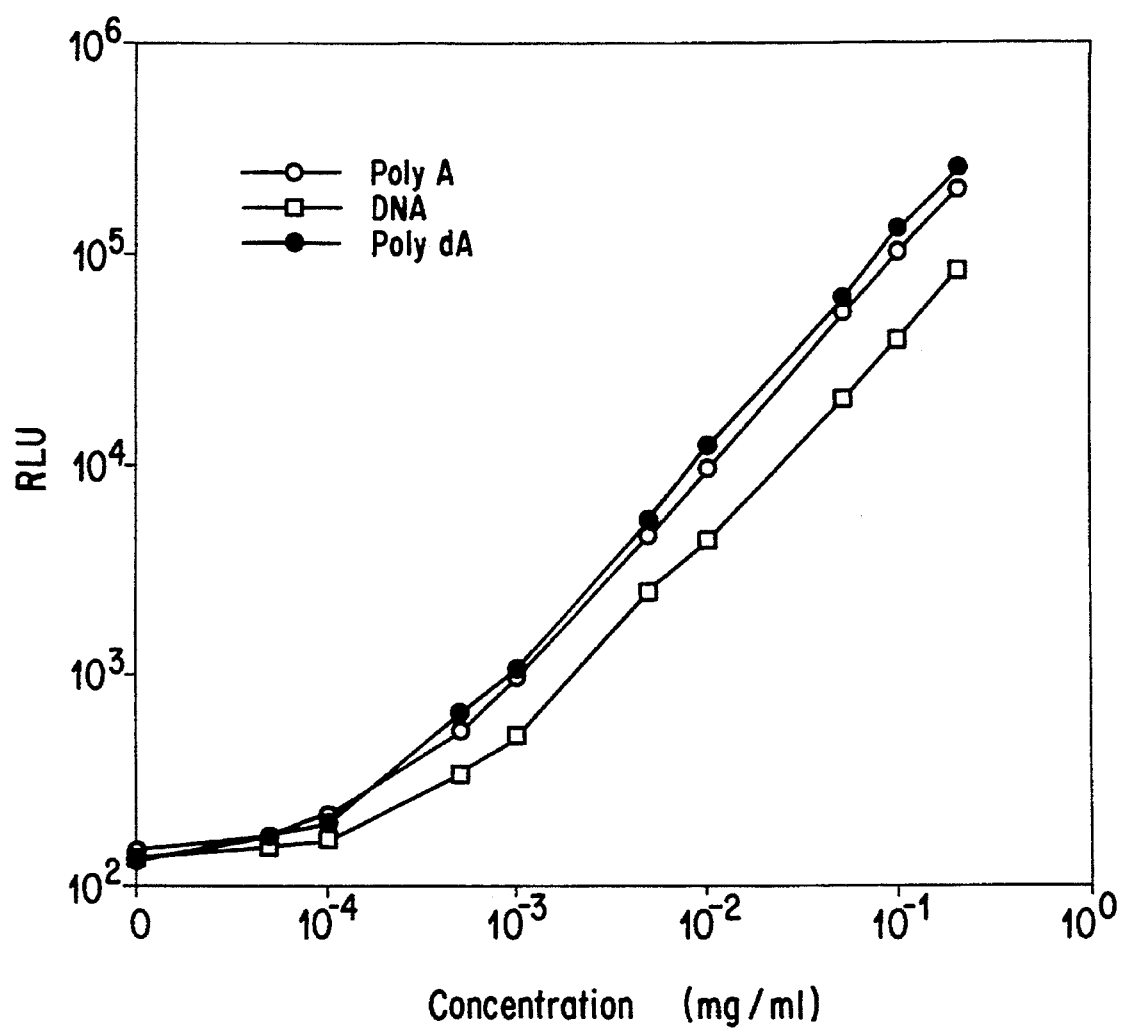
FIG. 3 is a graph showing calibration curves of DNA, poly A and poly dA when methytglyoxal dimethylacetal is used in the presence of tungstosilicic acid.

When calibration curves of DNA, poly A and poly dA were prepared from the thus obtained luminescence intensities, each of these curves showed a satisfactorily linear relationship within the range of from $1\times10^{-4}$ to 0.2 mg/ml as shown in FIG. 3. In the figure, the abscissa indicates concentrations of DNA, poly A and poly dA, and the ordinate indicates luminescence intensities at corresponding concentrations of DNA, poly A and poly dA.

Example 4

Effects of Heteropoly-acids on the Luminescence Reaction of Adenine i) Adenine was dissolved in a small amount of 0.1N hydrochloric acid and diluted with i-PrOH to prepare dilution samples of $1\times10^{-4}$, $5\times10^{-4}$ and $1\times10^{-3}$M. A 100 µl portion of each sample solution having a given concentration was put in a glass vial, followed by the addition of 50 µl of 0.4M methylglyoxal dimethylacetal (MGA) and the same volume of 0.196M tungstosilicic acid (dissolved in i-PrOH or 1.2N hydrochloric acid in i-PrOH), and the vial was then sealed and heated at 100° C. for 1 hour. The thus obtained reaction mixture were cooled, and the reaction solution to which tungstosilicic acid was added was used for the measurement of luminescent activity in the same manner as described in Example 1. Chemiluminescence of the other reaction solution to which hydrochloric acid has been added was measured in the following manner. A 10 µl portion of the reaction solution was put in a glass tube for measuring use and mixed with 400 µl of DMF containing 5 mM cysteine ethyl ester (CysE). The thus prepared sample tube was set in a chemiluminescence measuring apparatus, 300 µl of 0.25M sodium hydroxide aqueous solution was added to the tube to start the luminescence reaction and then the resulting luminescent activity (RLU) was measured for 2 seconds just after the addition of the reaction initiator.

Figure 4:
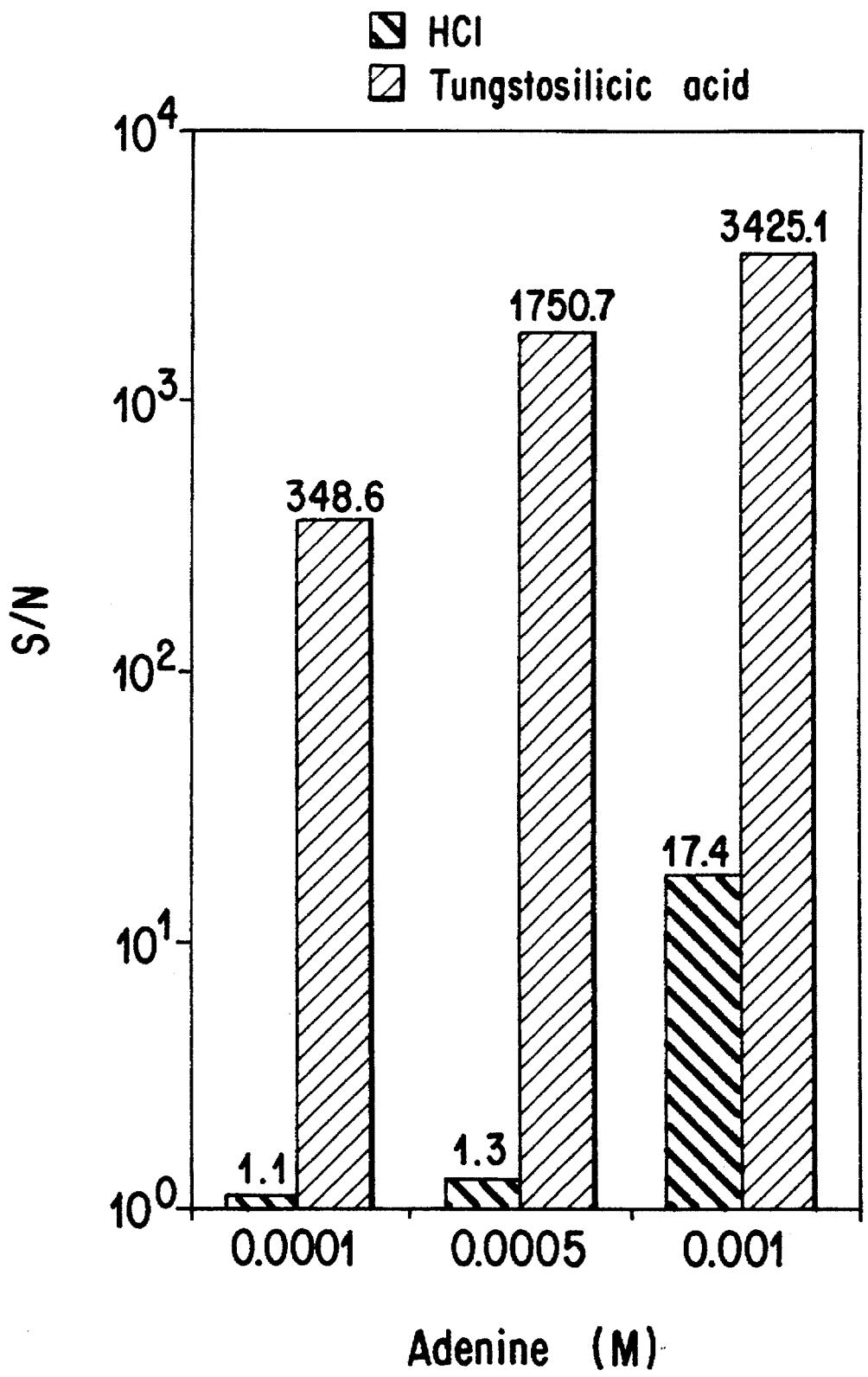
FIG. 4 is a graph showing improvement of signal to noise (S/N) ratio by tungstosilicic acid.

As shown in FIG. 4, when signal noise ratio (S/N ratio) was calculated from the thus obtained luminescence intensities, markedly increased S/N ratio was found in the reaction system in which tungstosilicic acid was used, in comparison with the reaction system that used hydrochlocic acid.

ii) Adenine was dissolved in a small amount of 0.1N hydrochloric acid and diluted with i-PrOH to prepare a sample solution of $1 \times 10^{-4}$M. A 100 µl portion of the sample solution was put in a glass vial. To this were added 50 µl of 0.4M methylglyoxal dimethylacetal (MGA) and the same volume of i-PrOH solution containing 0.196M of a heteropoly-acid or a heteropoly-acid salt, namely tungstosilicic acid (WSi), tungstophosphoric acid (WP), molybdophosphoric acid (MOP) or sodium molybdophosphoric acid (MoPNa). The thus prepared vial was then sealed and heated at 100° C. for 1 hour. As a control, a sample solution containing no adenine was treated in the same manner. Each of the thus obtained reaction mixtures was cooled and used for the measurement of luminescent activity (RLU) in the same manner as described in Example 1.

Figure 5:
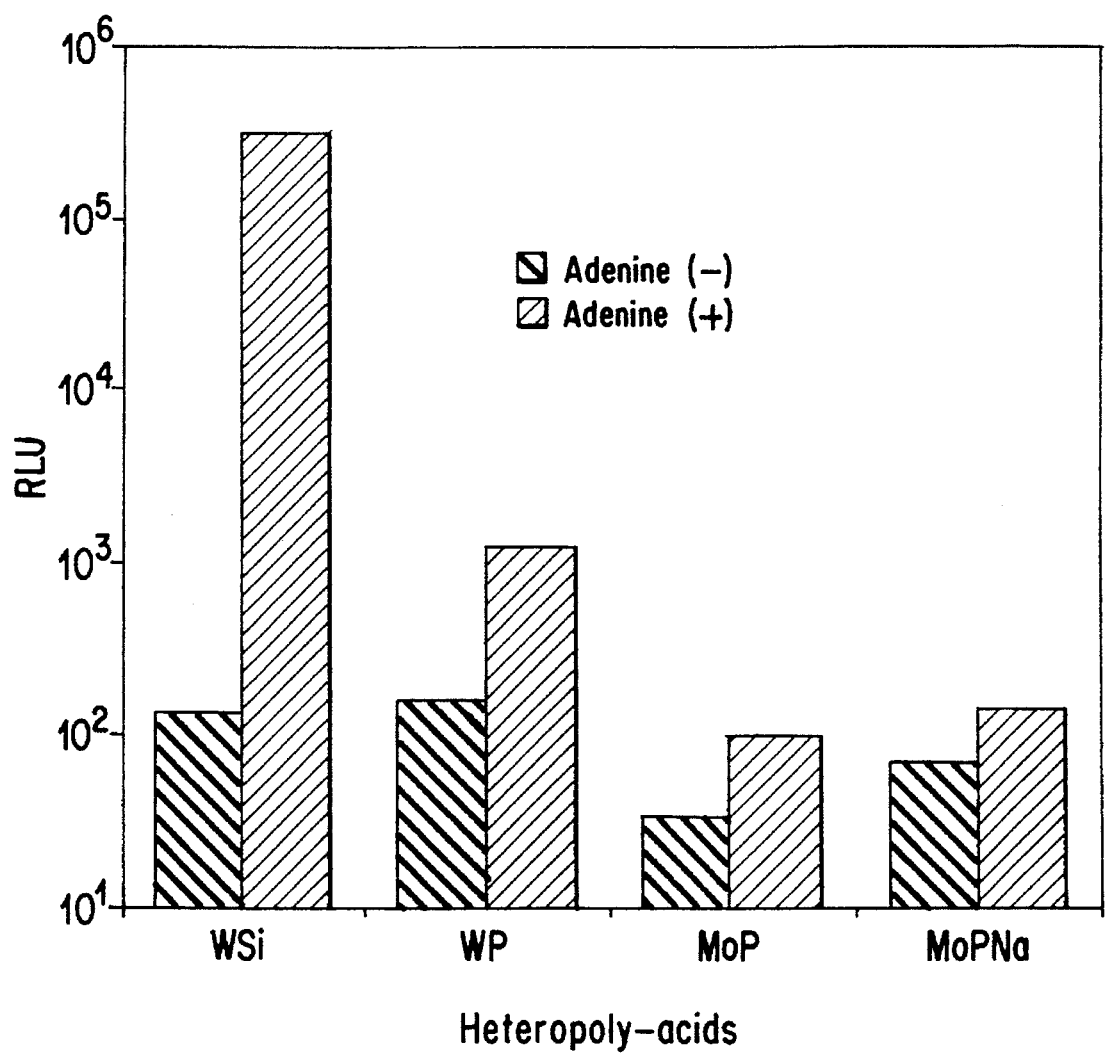
FIG. 5 is a graph showing comparison of the catalytic effects of various heteropoly-acids.

All of the 4 heteropoly-acids showed catalytic activity (FIG. 5). In the figure, adenine (+) indicates luminescence intensities of the adenine-added samples, and adenine (−) indicates luminescence intensities of the adenine-free control samples.

Example 5

Luminesence Reaction of Adenine Using Various Glyoxal Compounds i) An i-PrOH solution was prepared which contained 0.4M of each of 4 glyoxal derivatives, namely phenylglyoxal (PG), phenylglyoxal dimethylacetal (PGA) synthesized in accordance with the method of T. H. Chan et al. (*Synthesis*, 203–205 (1983)), p-methylphenylglyoxal (MPG) and p-fluorophenylglyoxal (FPG) synthesized in accordance with the method of M. Brawner Floyd et al. (*J. Org. Chem.*, 50, 5022–5027 (1985)). Separately from this, adenine was dissolved in a small amount of 0.1N hydrochloric acid and diluted with i-PrOH to prepare a sample of $1 \times 10^{-4}$M. A 100 µl portion of the sample solution was put in a glass vial, followed by the addition of 50 µl of the 0.4M glyoxal compound solution (PG, PGA, MPG or FPG) and the same volume of 0.196M tungstosilicic acid (dissolved in i-PrOH), and the vial was then sealed and heated at 100° C. for 1 hour. The thus obtained reaction mixture was cooled and used for the measurement of luminescent activity (RLU) in the same manner as described in Example 1.

Figure 6:
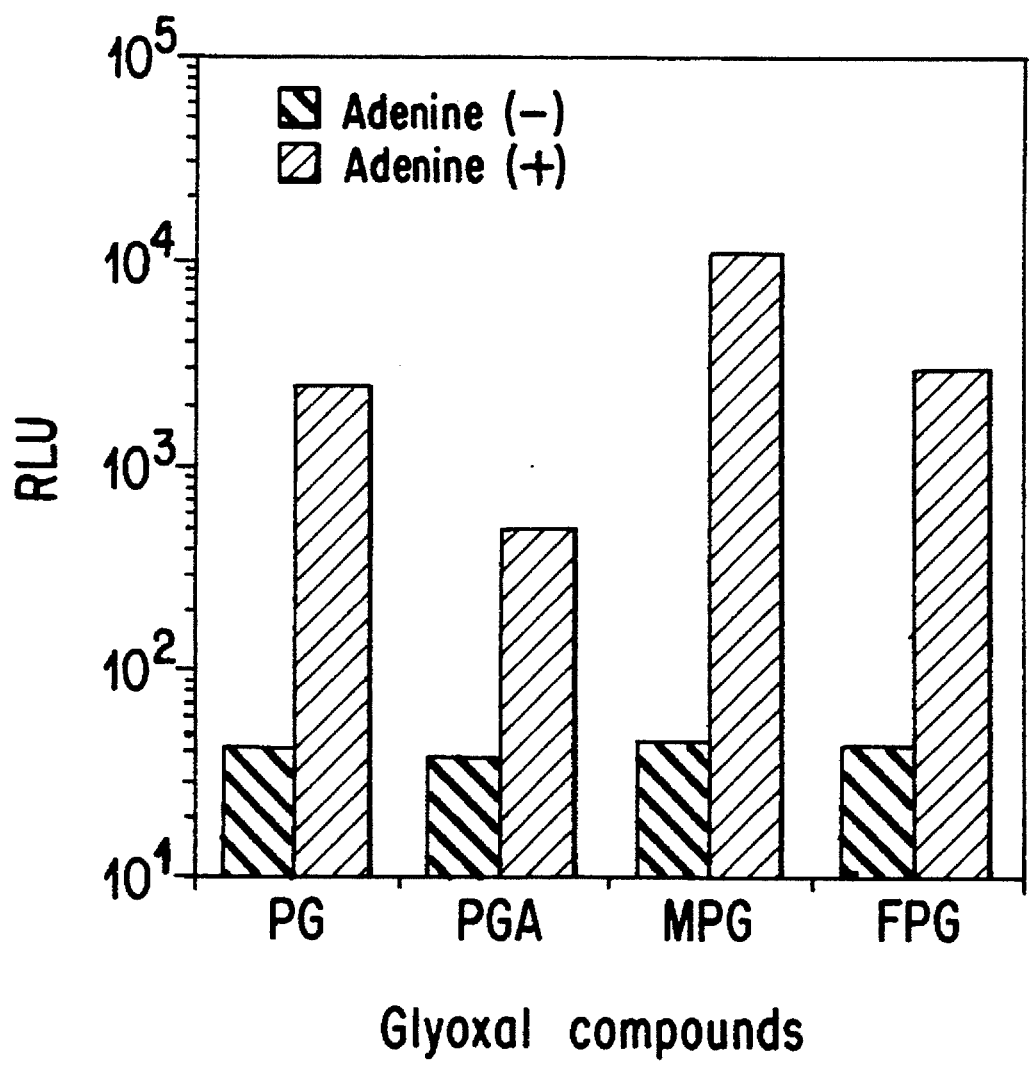
FIG. 6 is a graph showing reactivities of various glyoxal compounds with adenine in the presence of tungstosilicic acid.

As shown in FIG. 6, luminescence activity was found in all four of the reactions. In the figure, adenine (+) indicates luminescence intensity of an adenine-added sample, and adenine (−) indicates luminescence intensity of an adenine-free sample.

ii) An i-PrOH solution was prepared which contained 0.4M of each of 5 glyoxal derivatives, namely methytglyoxal (MG), methylglyoxal dimethylacetal (MGA) and ethylglyoxal dimethytacetal (EGA), n-butylglyoxal dimethylacetal (BuGA) and n-octylglyoxal dimethylacetal (OcGA) which have been synthesized in accordance with the method of Serrarosa (*Tetrahedron*, 16, 185–191, 1961)). Separately from this, adenine was dissolved in a small amount of 0.1N hydrochloric acid and diluted with i-PrOH to prepare a sample of $1 \times 10^{-4}$M. A 100 µl portion of the sample solution was put in a glass vial, followed by the addition of 50 µl of the 0.4M glyoxal compound solution (MG, MGA, EGA, BuGA or OcGA) and the same volume of 0.196M tungstosilicic acid (dissolved in i-PrOH), and the vial was then sealed and heated at 100° C. for 1 hour. As a control, a sample solution containing no adenine was treated in the same manner. The thus obtained reaction mixture was cooled and used for the measurement of luminescent activity (RLU) in the same manner as described in Example 1.

Figure 7:
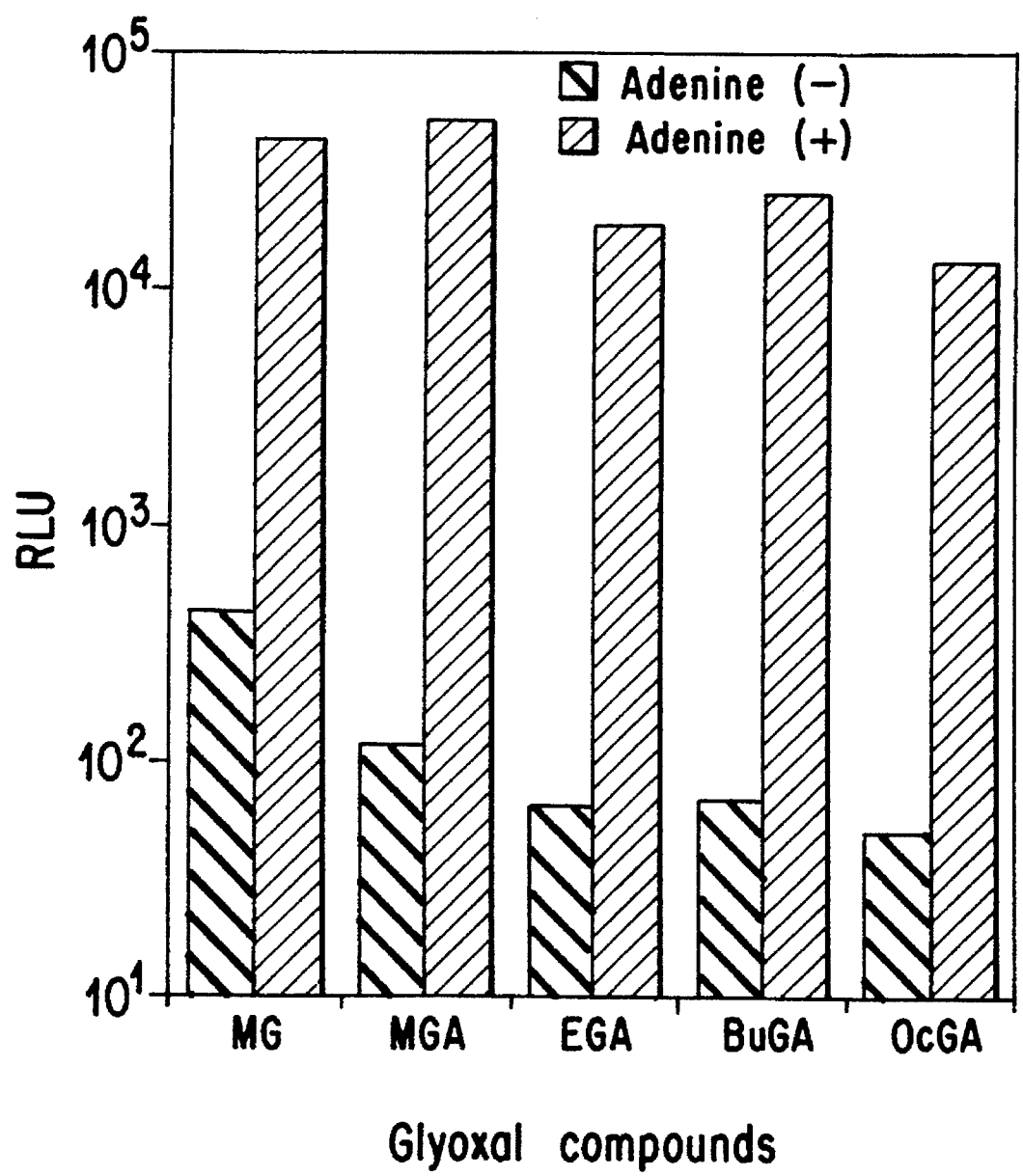
FIG. 7 is a graph showing reactivities of various glyoxal compounds with adenine in the presence of tungstosilicic acid.

As shown in FIG. 7, luminescence activity was found in all five of the reactions. In the figure, adenine (+) indicates luminescence intensity of an adenine-added sample, and adenine (−) indicates luminescence intensity of an adenine-free sample.

Example 6

Measurement of Various Nucleic Acid Bases Using Methylglyoxal Dimethylacetal i) As an adenyl group-containing substance, each of adenine, adenosine, adenylic acid, poly dA (manufactured by Pharmacia), poly A (manufactured by Pharmacia) and DNA (salmon sperm DNA, manufactured by Pharmacia) was dissolved in a small amount of distilled water and diluted with i-PrOH to prepare their sample solutions having the same absorbance at 260 nm. A 100 µl portion of each sample solution was put in a glass vial, followed by the addition of 50 µl of 0.4M methylglyoxal dimethylacetal (MGA) and the same volume of 0.196M tungstosilicic acid (dissolved in i-PrOH), and the vial was then sealed and heated at 100° C. for 1 hour. The thus obtained reaction mixture was cooled and used for the measurement of luminescent activity in the same manner as described in Example 1.

Figure 8:
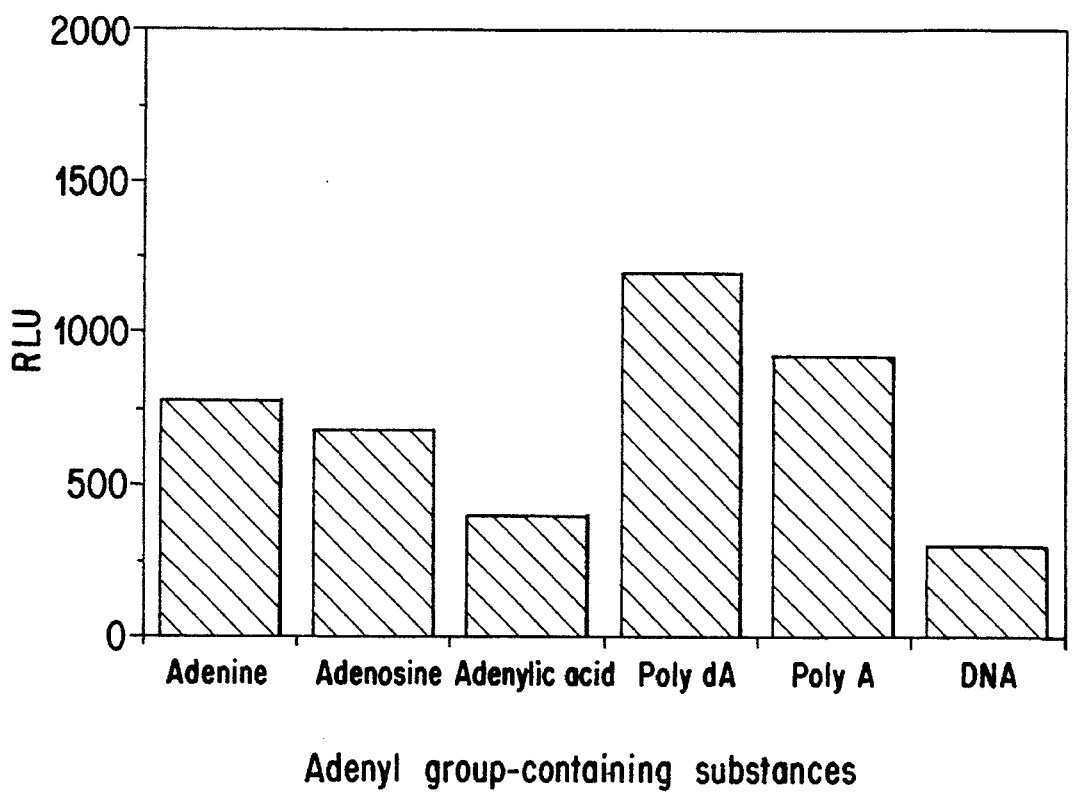
FIG. 8 is a graph showing reactivities of various nucleic acids and nucleic acid bases when methylglyoxal dimethylacetal is used in the presence of tungstosilicic acid.

As shown in FIG. 8, generation of luminescence was found in all of the reactions. In the figure, luminescent activity (RLU) of each reaction is expressed as a value per 1 absorbance at 260 nm of each sample solution.

ii) Guanine, thymine, cytosine, uracyl, guanosine, cytidine, thymidine and uridine were used as adenyl group-free substances, and each of the substances was dissolved in a small amount of 0.1N hydrochloric acid and diluted with i-PrOH to prepare a sample solution containing $5 \times 10^{-5}$M of each substance. A 100 µl portion of each sample solution was put in a glass vial, followed by the addition of 50 µl of 0.4M methylglyoxal dimethylacetal (MGA) and the same volume of 0.196M tungstosilicic acid (dissolved in i-PrOH), and the vial was then sealed and heated at 100° C. for 1 hour. The thus obtained reaction mixture was cooled and used for the measurement of luminescent activity (RLU) in the same manner as described in Example 1.

No generation of luminescence was observed in these reactions which include only substances which do not contain an adenyl group. The results are shown in Table 1 in which the RLU ratio means a ratio of RLU value of each test sample to 100 RLU of adenine obtained in 6-i). For the sake of comparison, the value of adenosine obtained in 6-i) is also shown in the table.

TABLE 1

| Compound | Conc. (mM) | RLU ratio | Compound | Conc. (mM) | RLU ratio |
|---|---|---|---|---|---|
| Adenine | 0.05 | 100 | Adenosine | 0.05 | 88 |
| Guanine | 0.05 | 0 | Guanosine | 0.05 | 0 |
| Cytosine | 0.05 | 0 | Cytidine | 0.05 | 0 |
| Thymine | 0.05 | 0 | Thymidine | 0.05 | 0 |
| Uracyl | 0.05 | 0 | Uridine | 0.05 | 0 |

Example 7

Effects of Sulfur Compounds in the Luminescence Solvent i) Adenine was dissolved in a small amount of 0.1N hydrochloric acid and diluted with i-PrOH to prepare a sample solution of $1\times 10^{-4}$M. A 100 μl portion of the sample solution was put in a glass vial, 50 μl of 0.4M methylglyoxal dimethylacetal (MGA) and the same volume of 0.196M tungstosilicic acid (dissolved in i-PrOH) were added to the sample solution, and the vial was then sealed and heated at 100° C. for 1 hour. The thus obtained reaction mixture was cooled and used for the measurement of chemiluminescence in the following manner. A 10 μl portion of the reaction mixture was put in a glass tube for measuring use and mixed with 400 μl of DMF containing 50 mM of hydrogen peroxide and 5 mM of any one of 2-mercaptoethanol (2-ME), hydroxyethyl disulfide (HDS), L-cysteine Cys), L-cysteine ethyl ester (CysE) and thioglycol (TG) or with the same volume of DMF containing 50 mM of hydrogen peroxide but no sulfur compound (NONE). After arranging the sample tube for measuring use in a chemiluminescence measuring apparatus (LB952T/16, manufactured by Berthold), 300 μl of distilled water was added to the tube to start the luminescence reaction, and the resulting luminescent activity (RLU) was measured for 2 seconds just after the addition of the reaction initiator.

Figure 9:
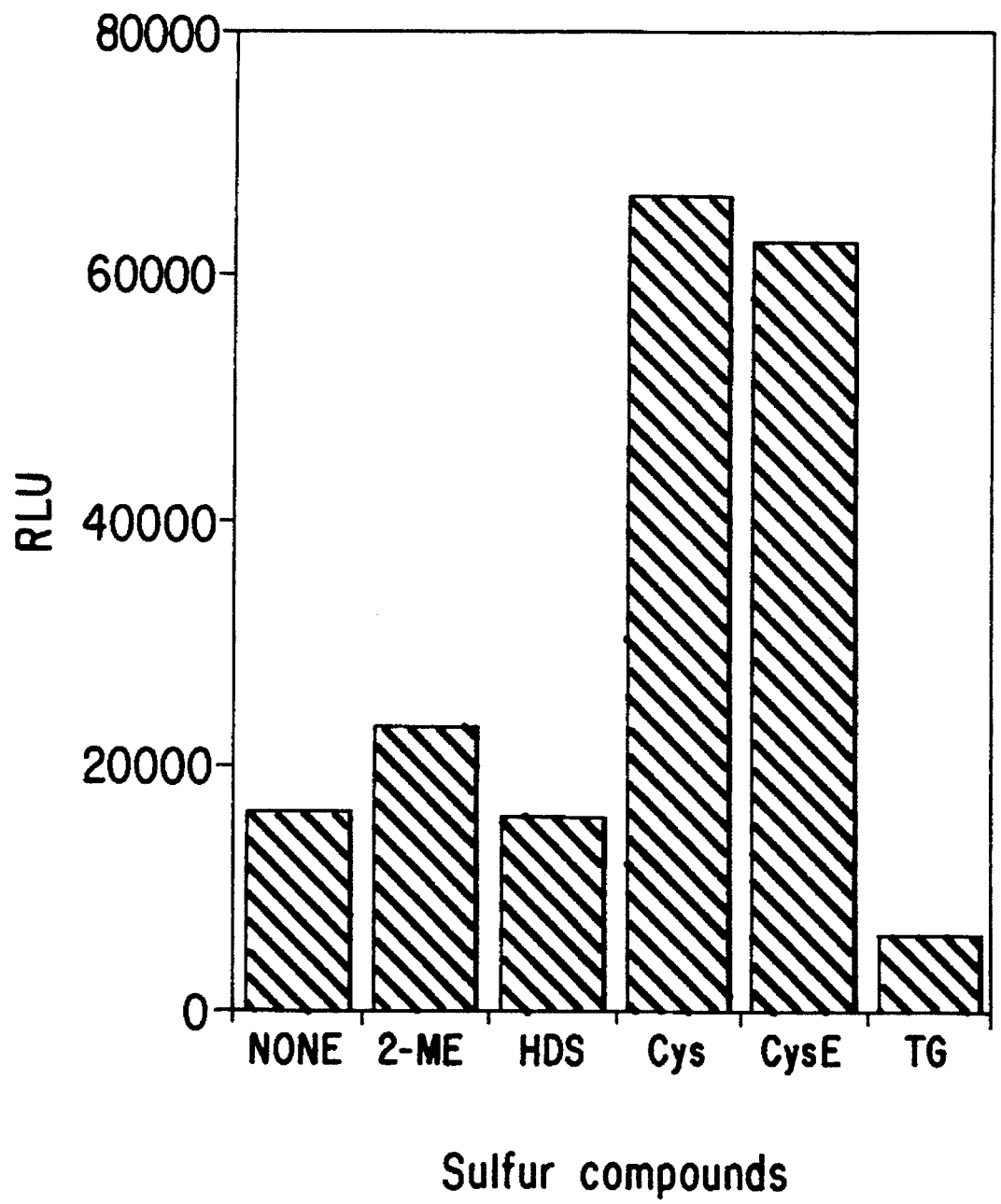
FIG. 9 is a graph showing comparison of the effect of various sulfur compounds in a luminescence solvent.

As shown in FIG. 9, a chemiluminescent reaction was obtained in every sulfur compound-added system and in the sulfur compound-free system, but the generation of luminescence was considerably intensified when L-cysteine (Cys) or L-cysteine ethyl ester (CysE) was added.

ii) Poly A was dissolved in a small amount of distilled water and diluted with i-PrOH to prepare a solution containing 0.2 mg/ml of the sample. A 100 μl portion of the sample solution was put in a glass vial, 50 μl of 0.4M methylglyoxal dimethylacetal (MGA) and the same volume of 0.196M tungstosilicic acid dissolved in i-PrOH were added to the sample solution, and the vial was then sealed and heated at 100° C. for 1 hour. The thus obtained reaction mixture was cooled and used for the measurement of chemiluminescence in the following manner. A 10 μl portion of the reaction mixture was put in a glass tube for measuring use and mixed with 400 μl of DMF containing 50 mM of hydrogen peroxide and 0.1 to 50 mM of L-cysteine ethyl ester (CysE). After arranging the sample tube for measuring use in a chemiluminescence measuring apparatus, 300 μl of distilled water was added to the tube to start the luminescence reaction, and the resulting luminescent activity (RLU) was measured for 2 seconds just after the addition of the reaction initiator.

Figure 10:
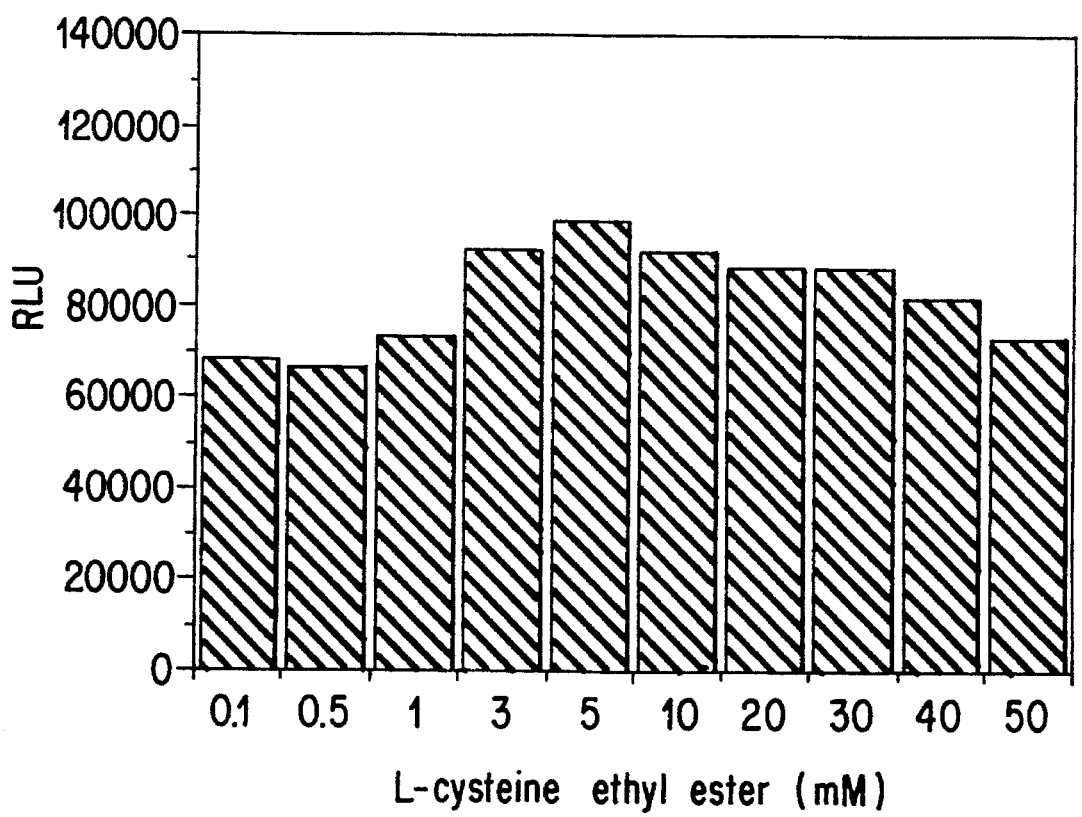
FIG. 10 is a graph showing the effect of the concentration of L-cysteine ethyl ester in a luminescence solvent.

As shown in FIG. 10, the highest luminescent activity was obtained when DMF solution of 5 mM L-cysteine ethyl ester (CysE) was added.

Example 8

Reaction Time of Methylglyoxal Dimethylacetal and Adenine

Adenine was dissolved in a small amount of 0.1N hydrochloric acid and diluted with i-PrOH to prepare a solution containing $1\times 10^{-3}$M in the sample. A 100 μl portion of the sample solution was put in a glass vial, 50 μl of 0.4M methylglyoxal dimethylacetal and the same volume of 0.196M tungstosilicic acid (dissolved in i-PrOH) were added to the sample solution, and the vial was then sealed and heated at 100° C. Portions of the reaction mixture were taken out periodically and cooled to measure the resulting luminescent activity (RLU) in the same manner as described in Example 1.

Figure 11:
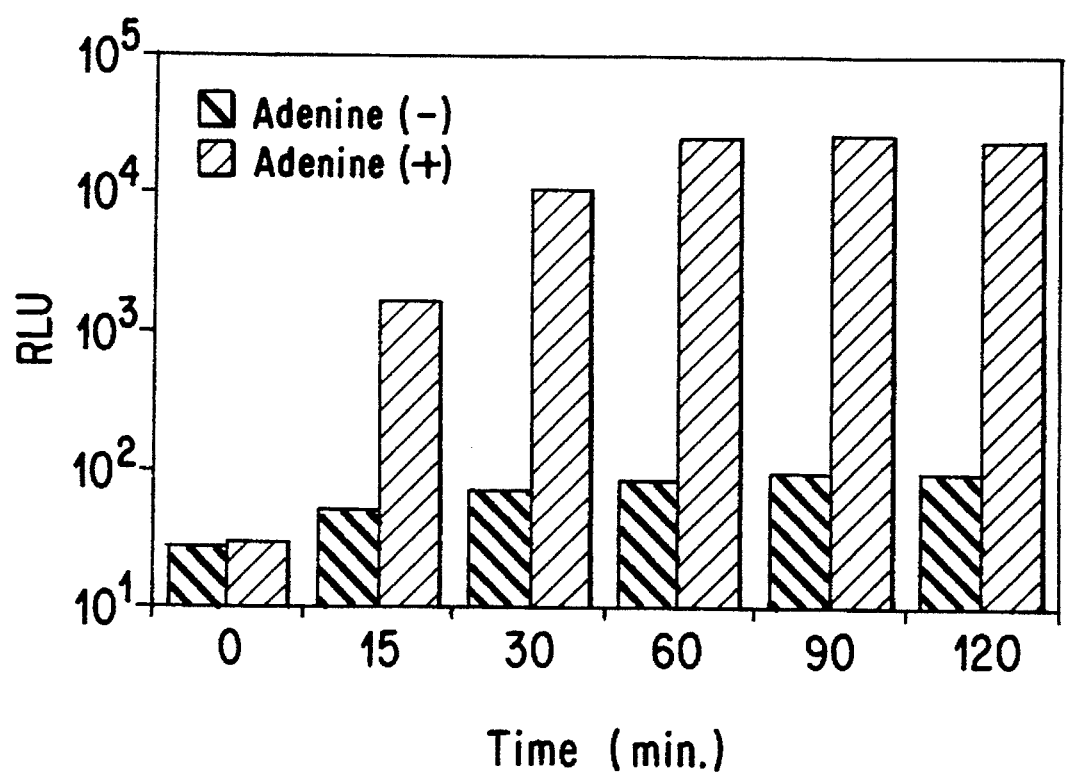
FIG. 11 is a graph showing a relationship between the reaction time and the quantity of luminescence when methytglyoxal dimethylacetal is reacted with adenine in the presence of tungstosilicic acid.

When relationship between luminescent activity and reaction time was examined based on the thus obtained luminescence intensities, it was found that the luminescence intensity reached its equilibrium state after 60 minutes of heating of the reaction solution (FIG. 11). In the figure, the abscissa indicates reaction period, and the ordinate indicates luminescence intensity of the reaction solution periodically taken out. Also, adenine (+) indicates luminescence intensity of the adenine-added sample, and adenine (−) indicates luminescence intensity of the adenine-free control sample.

Example 9

Measurement of Purified PCR Amplification Product Using Tungstosilicic Acid

Dane particles were purified from blood plasma of an HBe antigen-positive chronic type B hepatitis patient (serotype, adr) in accordance with the procedure of A. Fujiyama et al. (*Nucleic Acids Research*, p.4601, 11 (13), 1983) to isolate HBV-DNA (3.2 kb). The thus obtained DNA fragment was cloned into a plasmid (pBR 322), and the resulting recombinant plasmid (pBR-HBV) was purified. Using the primers B1 and B5R shown in Table 2 and a commercially available enzyme Tth-polymerase (manufactured by Toyobo), a 850 bp core region was amplified from the plasmid pBR-HBV. The thus obtained reaction solution was treated with phenol and chloroform and then subjected to gel filtration using NAP-10 (manufactured by Pharmacia). After carrying out ethanol precipitation in the usual way, the purified PCR amplification product was recovered by centrifugation and dissolved in distilled water, and its concentration was calculated based on its absorbance at 260 nm.

The thus purified PCR amplification product was diluted with distilled water to prepare serial dilutions of 0 to 500 ng/2 μl. A 2 μl portion of each dilution was put in a glass vial and evaporated to dryness by 2 minutes of heating at 100° C. To this were added 50 μl of 0.15M n-butylglyoxal dimethylacetal (BuGA) and the same volume of 0.196M tungstosilicic acid (WSi) (dissolved in i-PrOH). The vial was then sealed and heated at 100° C. for 1 hour. After cooling, a 10 μl portion of the thus obtained reaction mixture was put in a glass tube for measuring use and mixed with 400 μl of DMF containing 50 mM of hydrogen peroxide and 2 mM of cysteine. After arranging the sample tube for measuring use in a chemiluminescence analyzer, 300 μl of distilled water was added to the tube to start the luminescence reaction, and the resulting luminescent activity (RLU) was measured for 2 seconds just after the addition of the reaction initiator.

Figure 12:
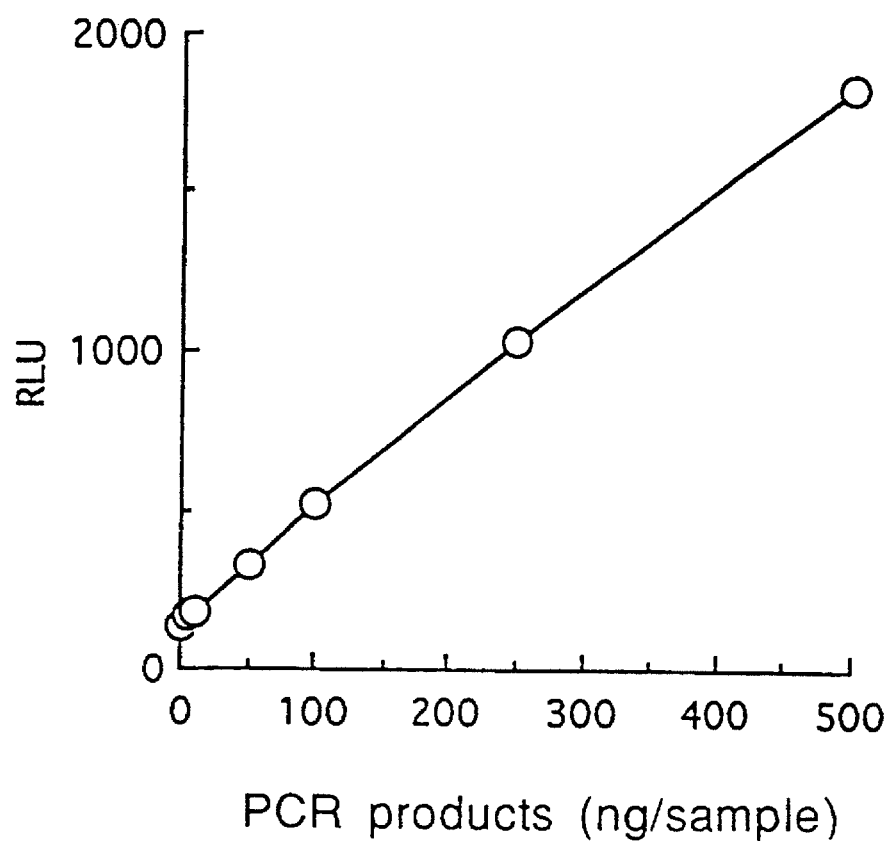
FIG. 12 is a graph showing a relationship between the amount of a PCR product and the quantity of chemiluminescence.

As shown in FIG. 12, the luminescence intensity increased in proportion to the amount of the PCR amplification product.

TABLE 2

| Primer | Sequence (5'-3') | Position | Amplified PCR product | Sequence ID No. |
|---|---|---|---|---|
| Sense B1 | $(T)_{10}$-CTCTGCCTAATCATCTCATG | 1701–1720 | chain length — | 1 |
| Anti-sense B5R | $(T)_{10}$-TAGGATAGAACCTAGCAGGC | 2511–2530 | 850 bp | 2 |

Example 10

Measurement of Nucleic Acid Using Tungstosilicic Acid

Figure 13:
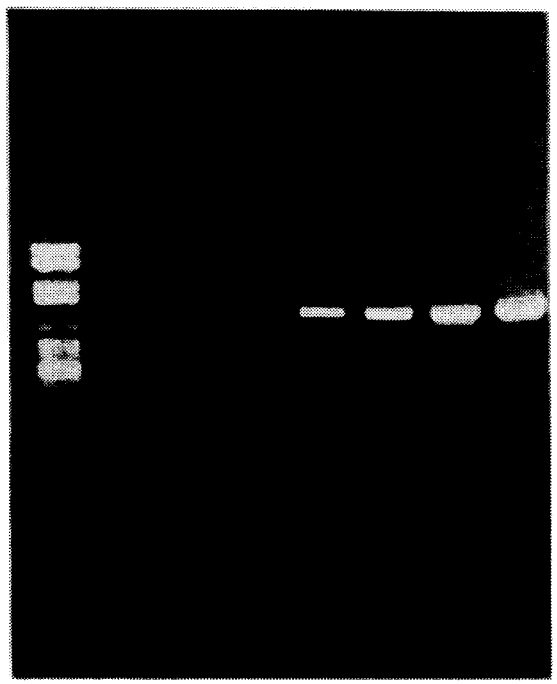
FIG. 13 is a photograph showing results of electrophoresis.

Using the same pBR-HBV as used in Example 9, serial dilutions of 0 to 1,000 pg/sample were prepared. Each of the thus prepared samples was subjected to 35 cycles of PCR using the primers B1 and B5R, each cycle consisting of 30 seconds of incubation at 94° C. 30 seconds at 55° C. and 30 seconds at 72° C. A 5 μl portion of each of the thus amplified reaction solutions was subjected to 1% agarose gel electrophoresis, and the band of interest was detected with ethidium bromide. As shown in FIG. 13, pBR-HBV was detectable at a minimum concentration of 1 pg/sample.

Next, a 50 μl portion of each of the reaction mixture was centrifuged using a centrifugation tube equipped with a membrane of 30,000 molecular weight cutoff (SUPREC-02, manufactured by Takara Shuzo), and the thus recovered PCR amplification product was washed with 100 μl of 70% i-PrOH and dissolved in 20 μl of distilled water. The entire portion of the resulting mixture was put in a glass vial and evaporated to dryness by 2 minutes of heating at 100° C. To this were added 50 μl of 0.15M n-butylglyoxal dimethylacetal (BuGA) and the same volume of 0.196M tungstosilicic acid (WSi) (dissolved in i-PrOH). The vial was then sealed and heated at 100° C. for 1 hour. After cooling, a 10 μl portion of the thus obtained reaction mixture was put in a glass tube for measuring use and mixed with 400 μl of DMF containing 50 mM of hydrogen peroxide and 2 mM of cysteine. After arranging the sample tube for measuring use in a chemiluminescence analyzer, 300 μl of distilled water was added to the tube to start the luminescence reaction, and the resulting luminescent activity (RLU) was measured for 2 seconds just after the addition of the reaction initiator.

Figure 14:
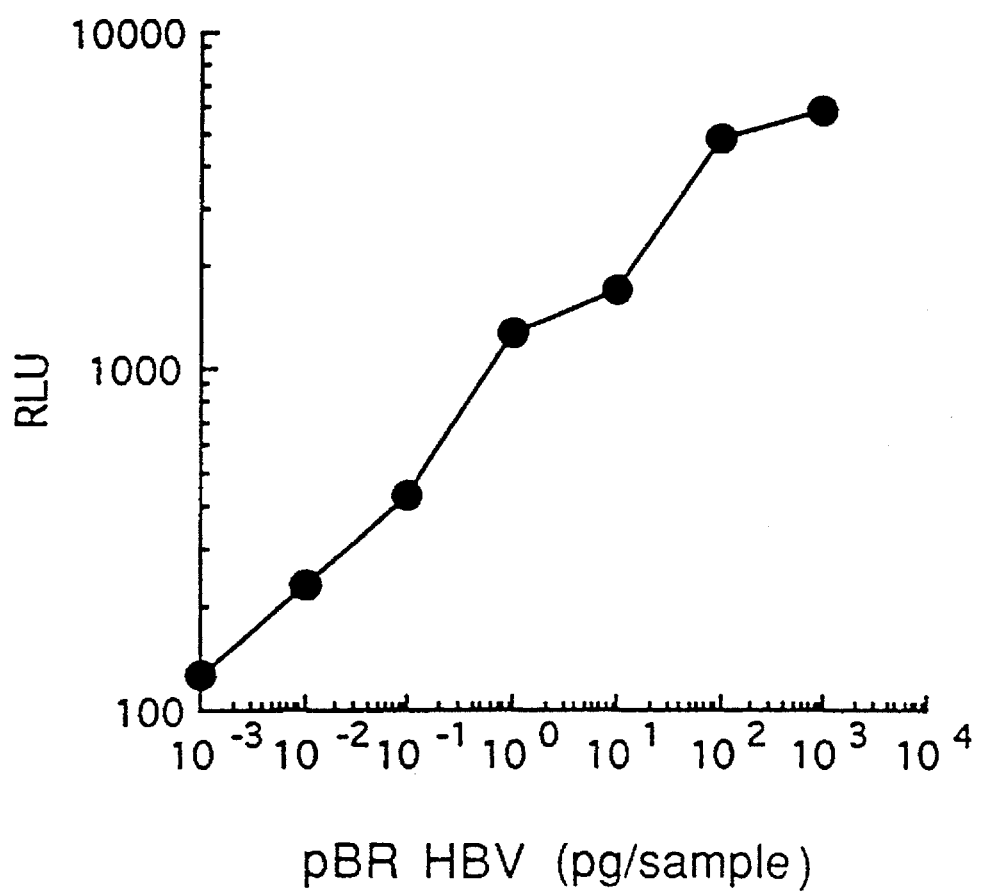
FIG. 14 is a graph showing a relationship between the amount of DNA in a sample and the luminous intensity of a PCR amplification product.

As shown in FIG. 14, a satisfactory dose/response curve was obtained within the range of from 0 to 100 pg pBR-HBV/sample. The detection sensitivity was 0.01 pg/sample or lower which was about 100 times higher than the detection sensitivity of the ethidium bromide-aided method.

Thus, it is apparent that high sensitivity and specific measurement of adenyl group-containing substances can be made by the measuring method of the present invention simply and easily with high S/N ratio.

What is claimed is:

1. A method for detecting the presence of or quantitating the amount of an adenyl group-containing substance which comprises:

i) deriving a chemiluminescent substance by reacting a compound represented by formula (1):

$$R^1\text{—CO—}R^2 \qquad (1)$$

wherein $R^1$ is a member selected from the group consisting of a hydrogen atom, an alkyl group having 1 to 12 carbon atoms, an alkenyl group having 1 to 12 carbon atoms, an alkynyl group having 1 to 12 carbon atoms, an aryl group having 1 to 18 carbon atoms and an aromatic heterocyclic group having 1 to 18 carbon atoms, wherein $R^1$ may be substituted or may form a condensed ring, and wherein $R^2$ is an aldehyde group or a group represented by the formula (2):

$$\text{—CH}(XR^3)(X'R^4) \qquad (2)$$

wherein X and X' are independently an oxygen atom or a sulfur atom, and $R^3$ and $R^4$ are independently selected from the group consisting of a hydrogen atom, an alkyl group having 1 to 12 carbon atoms, an alkenyl group having 1 to 12 carbon atoms, an alkynyl group having 1 to 12 carbon atoms and an aryl group having 1 to 16 carbon atoms, wherein $R^3$ and $R^2$ may be substituted or may form a condensed ring;

wherein $R^3$ and $R^4$ can optionally form a ring by binding;

with said adenyl group in the substance to be measured in the presence of a heteropolyacid or a salt thereof which is at least one compound selected from the group consisting of tungstosilicic acid, tungstophosphoric acid, tungstoarsenic acid, tungstogermanic acid, molybdosilicic acid, molybdophosphoric acid, molybdoarsenic acid, molybdogermanic acid, vanadophosphoric acid, and sodium, potassium and ammonium salts thereof, and ii) measuring chemiluminescence of the chemiluminescent substance in a luminescence solvent, thereby detecting the presence of or quantitating the amount of said adenyl group-containing substance.

2. A method according to claim 1, wherein said heteropolyacid or salt thereof is at least one compound selected from the group consisting of tungstosilicic acid, tungstophosphoric acid, tungstoarsenic acid, molybdosilicic acid, molybdophosphoric acid, molybdoarsenic acid, and sodium molybdophosphoric acid.

3. A method according to claim 2, wherein said heteropolyacid or salt thereof is at least one compound selected from the group consisting of tungstosilicic acid, tungstophosphoric acid, molybdophosphoric acid, and sodium molybdophosphoric acid.

4. A method according to any one of claims 1 to 3, wherein said substance to be measured is adenine, adenosine, an adenosine phosphate compound, DNA or RNA.

5. A method according to claim 1, wherein $R^1$ is selected from the group consisting of a hydrogen atom, an alkyl group having 1 to 8 carbon atoms, a phenyl group and an aromatic heterocyclic group having 1 to 8 carbon atoms, wherein $R^1$ may be substituted or may form a condensed ring, and wherein $R^3$ and $R^4$ are independently groups which are selected from the group consisting of a hydrogen atom, an alkyl group having 1 to 4 carbon atoms, and a phenyl group, wherein $R^3$ and $R^4$ may be substituted or may form a condensed ring, wherein $R^3$ and $R^4$ can optionally form a ring by binding.

6. A method according to claim 5, wherein said substance to be measured is adenine, adenosine, an adenosine phosphate compound, DNA or RNA.

7. A method according to claim 5, wherein said compound represented by formula (1) is a glyoxal derivative selected from the group consisting of methylglyoxal, methylglyoxal dimethylacetal, ethytglyoxal dimethylacetal, n-butylglyoxal dimethylacetal, n-octylglyoxal dimethylacetal, phenylglyoxal, phenylglyoxal dimethytacetal, p-methylphenylglyoxal and, p-fluorophenylglyoxal.

8. A method according to claim 7, wherein said substance to be measured is adenine, adenosine, an adenosine phosphate compound, DNA or RNA.

9. A method according to any one of claims 1 to 3, wherein chemiluminescence is measured by contacting said chemiluminescent substance with a reaction initiator in said luminescence solvent.

10. A method according to claim 9, wherein said luminescence solvent is at least one solvent selected from the group consisting of dimethylformamide, isopropanol, acetonitrile, dioxane, and dimethyl sulfoxide.

11. A method according to claim 1, wherein said compound of formula (1) is selected from the group consisting of n-alkyl glyoxal, phenylglyoxal, p-halophenylglyoxal, p-alkylphenylglyoxal, n-alkylglyoxal dimethylacetal, phenylglyoxal dimethylacetal, p-halophenylglyoXal dimethylacetal, and p-alkylphenylglyoxal dimethylacetal.

12. A method according to claim 3, wherein said compound of formula (1) is selected from the group consisting of n-alkyl glyoxal, phenylglyoxal, p-halophenylglyoxal, p-alkylphenylglyoxal, n-alkylglyoxal dimethylacetat, phenylglyoxal dimethylacetal, p-halophenylglyoxal dimethylacetal, and p-alkylphenylglyoxal dimethylacetal.

13. A method according to claim 3, wherein said compound of formula (1) is selected from the group consisting of methyl glyoxal, phenylglyoxal, methylglyoxal dimethylacetal, phenylglyoxal dimethylacetal, ethylglyoxal dimethylacetal, n-butylglyoxal dimethylacetal, p-methylphenylglyoxal, p-fluorophenylglyoxal and n-octylglyoxal dimethylacetal.

\* \* \* \* \*